United States Patent [19]
Denis et al.

[11] Patent Number: 5,380,938
[45] Date of Patent: Jan. 10, 1995

[54] PREPARATION OF UNSATURATED CARBOXYLIC ACIDS BY CARBONYLATION OF ALLYLIC BUTENOLS AND/OR ESTERS THEREOF

[75] Inventors: Philippe Denis, Decines; Francois Metz, Irigny; Carl Patois, Lyon; Robert Perron, Charly, all of France

[73] Assignee: Rhone-Poulenc Chimie, Courbevoie Cedex, France

[21] Appl. No.: 201,020

[22] Filed: Feb. 24, 1994

[30] Foreign Application Priority Data

Feb. 26, 1993 [FR] France .................. 93 02482

[51] Int. Cl.$^6$ ............................. C07C 57/02
[52] U.S. Cl. ..................................... 562/598
[58] Field of Search ................... 562/598; 560/209

[56] References Cited

U.S. PATENT DOCUMENTS

| | | | |
|---|---|---|---|
| 3,427,344 | 2/1969 | Tsuji et al. | 560/114 |
| 3,980,671 | 9/1976 | Fernholz et al. | 549/326 |
| 4,781,868 | 11/1988 | Langerbeins | 562/891 |
| 5,166,116 | 11/1992 | Drent et al. | 502/167 |
| 5,166,421 | 11/1992 | Bruner, Jr. | 562/522 |

FOREIGN PATENT DOCUMENTS 2180021 11/1973 France .

*Primary Examiner*—Arthur C. Prescott
*Attorney, Agent, or Firm*—Burns, Doane, Swecker & Mathis

[57] ABSTRACT

Unsaturated carboxylic acids, e.g., pentenoic acids, are prepared by carbonylating an allylic butenol and/or carboxylate ester thereof with carbon monoxide, in the presence of a catalytically effective amount of an iridium catalyst and an iodinated or brominated promoter therefor, and optionally, a copromoter, notably wherein the promoter/Ir molar ratio ranges from 0.1:1 to 20:1. The final product acids, e.g., 3-pentenoic acid, are themselves readily hydroxycarbonylated, for example, into adipic acid, via reaction with carbon monoxide and water.

23 Claims, No Drawings

PREPARATION OF UNSATURATED CARBOXYLIC ACIDS BY CARBONYLATION OF ALLYLIC BUTENOLS AND/OR ESTERS THEREOF

CROSS-REFERENCE TO COMPANION APPLICATION

Copending application Ser. No. 08/201,428, filed concurrently herewith and assigned to the assignee hereof.

BACKGROUND OF THE INVENTION

1. Field of the Invention

The present invention relates to the CO carbonylation of allylic butenols and/or of the carboxylic esters thereof.

2. Description of the Prior Art

U.S. Pat. No. 4,801,743 describes the carbonylation of allyl alcohol by carbon monoxide, in the presence of a palladium catalyst and a promoter therefor selected from among hydrogen fluoride, hydrogen chloride, hydrogen bromide and hydrogen iodide.

EP-A-0,428,979 describes the carbonylation of allylic butenols and esters thereof, in the presence of rhodium catalyst and a promoter selected from between hydrogen bromide and hydrogen iodide, the promoter/rhodium molar ratio ranging from 1:1 to 10:1.

SUMMARY OF THE INVENTION

A major object of the present invention is the provision of an improved process for the carbonylation of allylic butenols and or of the carboxylic esters thereof, to convert same into unsaturated carboxylic acids, and which comprises reacting carbon monoxide with at least one allylic butenol and/or carboxylic acid ester thereof, at elevated temperature, under a pressure greater than atmospheric pressure and in the presence of an iridium catalyst and of an iodinated or brominated promoter therefor, the promoter/iridium molar ratio ranging from 0.1:1 to 20:1.

DETAILED DESCRIPTION OF BEST MODE AND PREFERRED EMBODIMENTS OF THE INVENTION

More particularly according to the present invention, the activity of iridium catalysts in the subject process is indeed quite unexpected, because iridium is not known to catalyze the hydroxycarbonylation of butadiene, with palladium or rhodium catalysts typically being employed for such reaction.

The allylic butenols include 3-buten-2-ol, 2-buten-1-ol and mixtures thereof; the butenol esters which are useful in the process of the invention include, notably, the carboxylates of such butenols and, more particularly, those which are prepared from saturated or unsaturated aliphatic carboxylic acids having from 1 to 12 carbon atoms. Exemplary thereof are the allylic butenol esters of acetic acid, of propionic acid, of valeric acid, of adipic acid, and of pentenoic acids (2-pentenoic, 3-pentenoic and 4-pentenoic acids).

Preferably, the allylic butenols and/or the acetates, valerates or pentenoates thereof are suitable starting materials. In actual practice, when a butenol ester is used, esters of carboxylic acids are preferred which are formed over the course of the carbonylation reaction, such as valeric acid or 3-pentenoic acid.

The allylic butenols are compounds which are commercially available; they may also be easily prepared by hydration of butadiene. Their esters may be obtained by reacting said butenols or butadiene with the selected carboxylic acid. These syntheses of starting materials may be carried out extemporaneously, or in the carbonylation reactor itself.

Various sources of iridium can be used as the iridium catalyst required by the process of the invention. Exemplary of such sources of iridium are:
metallic Ir; $IrO_2$; $Ir_2O_3$;
$IrCl_3$; $IrCl_3 \cdot 3H_2O$;
$IrBr_3$; $IrBr_3 \cdot 3H_2O$;
$IrI_3$;
$Ir_2(CO)_4Cl_2$; $Ir_2(CO)_4I_2$;
$Ir_2(CO)_8$; $Ir_4(CO)_{12}$;
$Ir(CO) [P (C_6H_5)_3]_2I$;
$Ir(CO) [P (C_6H_5)_3]_2Cl$;
$Ir [P (C_6H_5)_3]_3I$;
$HIr[P(C_6H_5)_3]_3(CO)$;
$Ir(acac) (CO)_2$;
$[IrCl (cod)]_2$;
(acac=acetylacetonate; cod=1,5-cyclooctadiene).

The iridium catalysts which are preferred are $[IrCl(cod)]_2$, $Ir_4 (CO)_{12}$ and $Ir(acac) (CO)_2$.

The amount of catalyst to be used may vary over wide limits.

In general, an amount, expressed in moles of iridium metal per liter of reaction mixture, ranging from $10^{-4}$ to $10^{-1}$ provides satisfactory results. Smaller amounts may be used, but a slower reaction rate is, however, attained. Larger amounts present no disadvantages other than from an economic viewpoint.

The iridium concentration in the reaction mixture preferably ranges from $5 \times 10^{-4}$ to $5 \times 10^{-2}$ mol/liter.

By "iodinated or brominated promoter" is intended hydrogen iodide, hydrogen bromide and organoiodine and organobromine compounds which respectively generate hydrogen iodide and hydrogen bromide under the conditions of the reaction. Such organoiodine and organobromine compounds are more particularly alkyl iodides and bromides having from 1 to 10 carbon atoms, among which methyl iodide and methyl bromide are the preferred.

The promoter/Ir molar ratio preferably ranges from 1:1 to 10:1.

It is also within the scope of the invention to complement the subject catalyst system, i.e., the iridium catalyst and the promoter therefor, with an effective amount of a copromoter such as a metal iodide or a metal bromide, or else a metal carboxylate which is convertible, at least partially, into the corresponding iodide or bromide in the reaction mixture. Such copromoter is preferably an alkali metal iodide or bromide, or an alkali metal acetate. Thus, it is preferred, in particular with regard to the activity of the catalyst, to employ lithium iodide, sodium iodide, lithium bromide, sodium bromide, lithium acetate or sodium acetate. The copromoter/promoter molar ratio may vary very greatly, for example, from 0.01:1 to 100:1 and preferably from 0.1:1 to 50:1.

The reaction is carried out in the liquid phase. The temperature at which the reaction is carried out advantageously ranges from 50° C. to 250° C., and preferably from 80° C. to 200 C.

The total pressure at the reaction temperature may vary over wide limits. The partial pressure of the carbon monoxide, measured at 25° C. typically ranges from 0.5 bars to 100 bars, and preferably from 1 bar to 50 bars.

The carbon monoxide can be substantially pure carbon monoxide or technical-grade carbon monoxide, such as are commercially available.

The reaction for the carbonylation of allylic butenols and/or the esters thereof is generally carried out in an inert solvent medium.

Exemplary such solvents include the saturated or unsaturated aliphatic or aromatic carboxylic acids having not more than 20 carbon atoms, insofar as they are liquid under the reaction conditions. Representative of such carboxylic acids are acetic acid, propionic acid, butanoic acid, valeric acid, adipic acid, pentenoic acids, benzoic acid and phenylacetic acid. When an allylic butenol ester is carbonylated, it is preferred to employ a carboxylic acid solvent corresponding to the ester.

Other classes of solvents may also be used, especially saturated aliphatic or cycloaliphatic hydrocarbons and the chlorinated derivatives thereof, as they are also liquid under the reaction conditions. Exemplary of such solvents are benzene, toluene, chlorobenzene, dichloromethane, hexane and cyclohexane.

When it indeed is present in the reaction mixture, the solvent constitutes, for example, from 10% to 99% by volume relative to the total volume of the reaction mixture, and preferably from 30% to 90% by volume.

The carbonylation process according to the invention permits the preparation of pentenoic acids, in particular 3-pentenoic acid in the form of its cis- and trans-isomers, and to a lesser extent 2-pentenoic acid. These pentenoic acids may themselves be hydroxycarbonylated via reaction with carbon monoxide and water to provide adipic acid, one of the starting materials for the preparation of polyamide 66.

As the hydroxycarbonylation of pentenoic acids may advantageously be carried out in the presence of an iridium catalyst and of an iodinated or brominated promoter, it is possible, where appropriate, to conduct this second reaction directly, using the reaction mixture resulting from the carbonylation of the allylic butenols and/or the esters thereof, or after separation of the reaction byproducts, using the same apparatus. It is also possible to treat the reaction mixture according to any appropriate technique to separate the pentenoic acids obtained, the catalyst system, the solvent where present and the various byproducts formed.

The process of the invention may be carried out continuously or discontinuously.

In order to further illustrate the present invention and the advantages thereof, the following specific examples are given, it being understood that same are intended only as illustrative and in nowise limitative.

EXAMPLE 1

Into a 125 cm$^3$ autoclave purged beforehand with argon, there were successively introduced:

| | | |
|---|---|---|
| (i) | crotyl valerate (2-butenyl pentanoate): | 50 mmol |
| (ii) | valeric acid (PA): | 46 cm$^3$ |
| (iii) | hydrogen iodide (in aqueous solution at a concentration of 57% by weight: | 1.5 mmol |
| (iv) | [IrCl(cod)]$_2$: | 0.5 mmol |
| (v) | LiI: | 15 mmol |

The autoclave was sealed, placed in an oven incorporating agitation and connected to a supply of CO under pressure. 5 bars of CO were applied at 25° C., then the system was heated to 140° C. The pressure was adjusted at this temperature to 50 bars by means of CO (which corresponded to 36 bars of partial pressure of CO measured at 25° C.) and this pressure was maintained for 2 hours at 140° C.

The autoclave was then cooled and degassed, and the reaction mixture was analyzed by gas chromatography (GC).

The following results were obtained:

| | | |
|---|---|---|
| (a) | extent of conversion (EC) of crotyl valerate: | 35% |
| (b) | yield of 3-pentenoic acid (P3) relative to the crotyl valerate charged (RY): | 24% |

Other compounds were identified by GC:
(1) 2-methyl-3-butenoic acid (MBE),
(2) 2-methylbutanoic acid (MBA),
(3) butenes (C4),
(4) valeric acid.

EXAMPLE 2

The procedure of Example 1 was repeated, except that the hydrogen iodide and lithium were replaced by 1.5 mmol of hydrogen bromide.

The following results were obtained:

| | | |
|---|---|---|
| (a) | EC of crotyl valerate: | 80% |
| (b) | RY of P3: | 40% |

EXAMPLES 3 TO 7

The procedure of Example 1 was repeated employing variable amounts of hydrogen iodide and lithium iodide (reported in the Table below). In addition, Example 7 was carried out at 185° C. instead of 40° C. The results obtained are also reported in the Table below:

TABLE

| Examples | HI (mmol) | LiH (mmol) | % EC of crotyl valerate | % RY P3 | % RY MBE + MBA | % RY C4 |
|---|---|---|---|---|---|---|
| Example 3 | 1.5 | 0 | 48 | 16 | 20 | 15 |
| Example 4 | 4.0 | 15 | 63 | 29 | 5 | 7 |
| Example 5 | 0.5 | 15 | 48 | 10 | 4 | 6 |
| Example 6 | 1.5 | 30 | 70 | 24 | 4 | 12 |
| Example 7 | 1.5 | 0 | 80 | 17 | 13 | 18 |

EXAMPLE 8

The procedure of Example 1 was repeated, but replacing the crotyl valerate by 2-buten-1-ol (or crotyl alcohol) and omitting the lithium iodide.

The following results were obtained:

| | | |
|---|---|---|
| (a) | EC of 2-buten-1-ol: | 100% |
| (b) | RY of P3: | 24% |

EXAMPLE 9

Into a 125 cm$^3$ autoclave purged beforehand with argon, there were successively introduced:

| (i) | 2-butenyl-3-pentenoate: | 50 mmol |
| (ii) | acetic acid: | 46 cm$^3$ |
| (iii) | hydrogen bromide: | 1.5 mmol |
| (iv) | [IrCl(cod)]$_2$: | 0.5 mmol |
| (v) | NaCH$_3$COO: | 3 mmol |

The autoclave was sealed, placed in an oven incorporating agitation and connected to a supply of CO under pressure 5 bars of CO were applied at 25° C., then the system was heated to 140° C. The pressure was adjusted at this temperature to 50 bars using CO (which corresponded to 36 bars of partial pressure of CO measured at 25° C.), and this pressure was maintained for hour, 30 min at 140° C.

The autoclave was then cooled and degassed, and the reaction mixture was analyzed by gas chromatography (GC).

The following results were obtained:

| (a) | EC of 2-butenyl-3-pentenoate: | 31% |
| (b) | RY of P3: | 15% |
| (c) | RY of C4: | 4% |
| (d) | RY of butadiene: | 1% |
| (e) | RY of C6 diacids: | 1% |

EXAMPLE 10 (COMPARATIVE)

Into a 125 cm$^3$ autoclave purged beforehand with argon, there were successively introduced:

| (i) | butadiene: | 80 mmol |
| (ii) | water: | 90 mmol |
| (iii) | valeric acid: | 46 cm$^3$ |
| (iv) | hydrogen iodide: | 1.5 mmol |
| (v) | [IrCl(cod)]$_2$: | 0.5 mmol |

The autoclave was sealed, placed in an oven incorporating agitation, and connected to a supply of CO under pressure. 5 bars of CO were applied at 25° C., then the system was heated to 140° C. The pressure was adjusted at this temperature to 50 bars using CO (which corresponded to 36 bars of partial pressure of CO measured at 25° C.), and this pressure was maintained for hours at 140° C.

The autoclave was then cooled and degassed, and the reaction mixture was analyzed by gas chromatography (GC).

The following results were obtained:

| (a) | EC of butadiene: | 100% |
| (b) | RY of P3: | 6% |
| (c) | RY of C4: | 32% |
| (d) | RY of valeric acid: | 6% |
| (e) | RY of MBA + MBE: | 9% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an unsaturated carboxylic acid, comprising reacting an allylic butenol and/or carboxylate ester thereof with carbon monoxide, in the presence of a catalytically effective amount of an iridium catalyst and an iodinated or brominated promoter therefor.

2. The process as defined by claim 1, wherein the promoter/Ir molar ratio ranges from 0.1:1 to 20:1.

3. The process as defined by claim 1, comprising reacting 3-buten-2-ol, 2-buten-1-ol, or mixture thereof, with carbon monoxide.

4. The process as defined by claim 1, comprising reacting a carboxylate ester of an allylic butenol with carbon monoxide.

5. The process as defined by claim 4, said carboxylate ester being of a saturated or unsaturated aliphatic carboxylic acid having from 1 to 12 carbon atoms.

6. The process as defined by claim 5, said carboxylate ester comprising an allylic butenol ester of acetic acid, propionic acid, valeric acid, adipic acid, or pentenoic acid.

7. The process as defined by claim 1, said iridium catalyst comprising metallic Ir, IrO$_2$, Ir$_2$O$_3$, IrCl$_3$, IrCl$_3$. 3H$_2$O, IrBr$_3$, IrBr$_3$. 3H$_2$O, IrI$_3$, Ir$_2$(CO)$_4$Cl$_2$; Ir$_2$(CO)$_4$I$_2$, Ir$_2$(CO)$_8$, Ir$_4$(CO)$_{12}$; Ir(CO)[P(C$_6$H$_5$)$_3$]$_2$I , Ir(CO) [P(C$_6$H$_5$)$_3$]$_2$Cl, Ir[P(C$_6$H$_5$)$_3$]$_9$ $_3$I, HIr[P(C$_6$H$_5$)$_3$]$_3$.(CO), Ir(acac) (CO)$_2$, or [IrCl(cod)]$_2$, wherein acac is acetylacetonate and cod is 1,5-cyclooctadiene).

8. The process as defined in claim 1, wherein the amount of iridium catalyst, expressed in moles of iridium metal per liter of reaction mixture, ranges from $10^{-4}$ to $10^{-1}$ mol/liter.

9. The process as defined by claim 8, said amount of iridium catalyst ranging from $5 \times 10^{-4}$ to $5 \times 10^{-2}$ mol/liter.

10. The process as defined by claim 1, said iodinated or brominated promoter comprising hydrogen iodide, hydrogen bromide, or organoiodine or organobromine compound precursor thereof.

11. The process as defined by claim 2, said promoter/Ir molar ratio ranging from 1:1 to 10:1.

12. The process as defined by claim 1, carried out in the further presence of an effective amount of a copromoter for said iridium catalyst.

13. The process as defined by claim 12, said copromoter comprising a metal iodide, metal bromide, or metal carboxylate precursor thereof.

14. The process as defined by claim 12, said copromoter comprising an alkali metal iodide, bromide or acetate.

15. The process as defined by claim 12, wherein the copromoter/promoter molar ratio ranges from 0.01:1 to 100:1.

16. The process as defined by claim 15, said copromoter/promoter molar ratio ranging from 0.1:1 to 50:1.

17. The process as defined by claim 1, carried out in the liquid phase, at a temperature ranging from 50° C. to 250° C., under a partial pressure of carbon monoxide, measured at 25° C., ranging from 0.5 bar to 100 bars.

18. The process as defined by claim 17, carried out at a temperature ranging from 80° C. to 200° C., and under a partial pressure of carbon monoxide ranging from 1 bar to 50 bars.

19. The process as defined by claim 1, carried out in an inert liquid solvent medium.

20. The process as defined by claim 19, said liquid solvent comprising a saturated or unsaturated aliphatic or aromatic carboxylic acid having not more than 20 carbon atoms, or a saturated aliphatic or cycloaliphatic hydrocarbon or chlorinated derivative thereof.

21. The process as defined by claim 20, said liquid solvent comprising from 10% to 99% by volume of the total volume of the reaction mixture.

22. The process as defined by claim 21, said liquid solvent comprising from 30% to 90% by volume of the total volume of the reaction mixture.

23. The process as defined by claim 19, said liquid solvent comprising acetic acid, propionic acid, butanoic acid, valeric acid, adipic acid, a pentenoic acid, benzoic acid, phenylacetic acid, benzene, toluene, chlorobenzene, dichloromethane, hexane, or cyclohexane.

* * * * *